US012642694B2

(12) United States Patent
Son et al.

(10) Patent No.: US 12,642,694 B2
(45) Date of Patent: Jun. 2, 2026

(54) HEAD COOLING DEVICE

(71) Applicant: mpacplus Co., Ltd., Seoul (KR)

(72) Inventors: Kwang Oh Son, Seoul (KR); Sang Yeol Son, Seoul (KR)

(73) Assignee: MPACPLUS CO., LTD., Seoul (KR)

( * ) Notice: Subject to any disclaimer, the term of this patent is extended or adjusted under 35 U.S.C. 154(b) by 278 days.

(21) Appl. No.: 18/544,836

(22) Filed: Dec. 19, 2023

(65) Prior Publication Data

US 2024/0307218 A1     Sep. 19, 2024

(30) Foreign Application Priority Data

| | | |
|---|---|---|
| Mar. 14, 2023 | (KR) | 10-2023-0033391 |
| Mar. 14, 2023 | (KR) | 10-2023-0033404 |
| Aug. 24, 2023 | (KR) | 10-2023-0111206 |

(51) Int. Cl.
*A61F 7/02*       (2006.01)
*A61F 7/00*       (2006.01)

(52) U.S. Cl.
CPC ........ *A61F 7/02* (2013.01); *A61F 2007/0008* (2013.01); *A61F 2007/0098* (2013.01); *A61F 2007/0215* (2013.01); *A61F 2007/0268* (2013.01)

(58) Field of Classification Search
CPC ...... A61F 2007/0008; A61F 2007/0098; A61F 2007/0215; A61F 2007/0268
USPC .................................. 607/110, 108, 109, 114
See application file for complete search history.

(56) References Cited

U.S. PATENT DOCUMENTS

| | | | | | |
|---|---|---|---|---|---|
| 2,049,723 | A | * | 8/1936 | Pomeranz | A61F 7/103 607/110 |
| 2,566,533 | A | * | 9/1951 | Poux | A61F 7/02 156/146 |
| 2,602,302 | A | * | 7/1952 | Poux | F25D 3/08 62/530 |
| 3,349,825 | A | * | 10/1967 | Andreadis | A61F 7/08 383/96 |

(Continued)

FOREIGN PATENT DOCUMENTS

| | | |
|---|---|---|
| JP | 2000-060892 A | 2/2000 |
| JP | 2002-309429 A | 10/2002 |

(Continued)

OTHER PUBLICATIONS

The Wayback Machine—https://web.archive.org/web/20230307111234/ https://www.makuake.com/project/suolife.

*Primary Examiner* — Linda C Dvorak
(74) *Attorney, Agent, or Firm* — LRK PATENT LAW FIRM

(57) ABSTRACT
A head cooling device includes a central portion that has a predetermined volume of space and is seated on a top portion of the user's head; and a plurality of wing portions radially connected to the central portion and extending in a fan shape, wherein each of the wing portions includes a plurality of chambers each having a predetermined volume of space in which a phase change material is charged, and a plurality of bridges configured to partition and connect each of the plurality of chambers. The central portion and each of the plurality of chambers further incudes a cushioning member to protect the user's head and improve safety by absorbing and alleviating an impact applied from outside.

19 Claims, 15 Drawing Sheets

(56)          References Cited

U.S. PATENT DOCUMENTS

| | | | | |
|---|---|---|---|---|
| 4,552,149 | A * | 11/1985 | Tatsuki | A61F 7/10 607/110 |
| 7,028,344 | B2 * | 4/2006 | Toth | A42B 3/122 2/171.2 |
| 7,264,630 | B1 * | 9/2007 | Webb | A61F 7/02 607/108 |
| 8,172,888 | B1 * | 5/2012 | Beavers | A61F 7/02 607/104 |
| 8,529,613 | B2 * | 9/2013 | Radziunas | A61F 7/10 62/259.3 |
| 2002/0058976 | A1 * | 5/2002 | Lee | A61F 7/10 607/110 |
| 2007/0277806 | A1 * | 12/2007 | Dodo | C09K 5/18 126/263.02 |
| 2010/0083421 | A1 * | 4/2010 | Cho | F25D 3/08 62/530 |
| 2013/0211484 | A1 * | 8/2013 | Rozental | A61F 7/10 607/110 |
| 2014/0020158 | A1 | 1/2014 | Parsons et al. | |
| 2014/0303699 | A1 * | 10/2014 | Wahl | A61F 7/02 607/110 |
| 2017/0239083 | A1 * | 8/2017 | Unver | A61F 7/02 |
| 2018/0042331 | A1 | 2/2018 | Bologna et al. | |
| 2018/0049914 | A1 * | 2/2018 | Stewart | A61F 7/02 |
| 2019/0336330 | A1 * | 11/2019 | Hickey | A61F 7/10 |

FOREIGN PATENT DOCUMENTS

| | | |
|---|---|---|
| JP | 2004-003111 A | 1/2004 |
| JP | 2005-273119 A | 10/2005 |
| JP | 2007-217846 A | 8/2007 |
| JP | 2017-000755 A | 1/2017 |
| JP | 2021-088784 A | 6/2021 |
| KR | 10-2007-0014248 A | 2/2007 |
| KR | 10-2010-0052863 A | 5/2010 |
| KR | 10-1424384 B1 | 8/2014 |
| KR | 10-2021-0007226 A | 1/2021 |
| KR | 10-2022-0135601 A | 10/2022 |
| KR | 10-2022-0148633 A | 11/2022 |

* cited by examiner

HEAD COOLING DEVICE

CROSS-REFERENCE TO RELATED APPLICATIONS

This application claims priorities to Korean Patent Application Nos. 10-2023-0033391 and 10-2023-0033404, filed on Mar. 14, 2023, and Korean Patent Application No. 10-2023-0111206, filed on Aug. 24, 2023, which are incorporated herein by reference in their entireties.

BACKGROUND

1. Field of the Disclosure

The present disclosure relates to a head cooling device, and more particularly to a head cooling device that enhances a cooling effect on a user's head and protects the user's head from an external impact.

2. Description of Related Art

In general, a cap is worn to block sunlight, or a helmet is worn on a user's head to prevent injury from collisions with surrounding objects or falling objects when riding a bicycle or a motorcycle, playing strenuous sports or leisure activities, military training, or working at work sites.

When people are exposed to a high-temperature surroundings, e.g., outdoor activities or outdoor works in summer, construction works in desert areas, medical or quarantine activities, or indoor-works exposed to high temperatures near a metal melting furnace, a temperature inside the helmet worn by the user rises quickly.

In particular, in a case that the helmet has a poor ventilation ability, the temperature of the user's head, which is maintained at a relatively high in the user's body, rises rapidly, reducing work efficiency, affecting a user's health condition, or becoming an obstacle to safe activities or work performances. In a worse case, it leads to a state that requires a quick medical treatment.

Moreover, as a temperature in summer gradually rises due to a global warming, heat waves continue and the number of patients with heat-related illnesses increases, which requires establishment of solutions on health and safety issues to the patients.

To alleviate problems caused by a temperature increase of the user's head as described above, head cooling devices with various shapes and structures have been developed and applied hitherto.

A conventional head cooling device generally has a bendable disk shape where a phase change material (PCM), which changes a phase between a solid state and a liquid state at room temperature, is filled into a plurality of chambers each having a predetermined volume of space, and a ventilation portion is formed for an air flow between the plurality of chambers.

When the head cooling device is maintained below a phase change temperature (a melting point or a solidification point) of the PCM charged in the chamber for a predetermined period of time, the PCM in a liquid state is changed to a frozen solid state. The head cooling device in which the PCM has been solidified is then placed on a top portion of the user's head or coupled to an inner portion of the helmet and becomes brought into contact with the user's head. Therefore, as the PCM absorbs a heat around the user's head, it melts and changes from the solid state to the liquid state, providing a cooling effect (coolness) to the user's head.

However, the conventional head cooling device has a disadvantage that the cooling effect is reduced due to a poor contact with the user's head along an outer circumference surface of the head.

In addition, to increase contact with the user's head, a separate pressing member has been provided at the helmet and a coupling member is further installed to connect the pressing member to the head cooling device, which makes a structure of the head cooling device complicate.

Meanwhile, in a case of a head cooling device adopting a thin cooling sheet with a plurality of chambers each having a predetermined space of volume, since an amount of the PCM charged in the chamber is not much, the PCM tends to be melt (liquefied) quickly, thereby shortening a duration period of a cooling operation by the PCM. Accordingly, there is an inconvenience that the cooling sheet with the liquefied PCM should be frequently replaced with a new cooling sheet having the solidified PCM.

To avoid frequent replacement of the cooling sheet, in a case that the amount of PCM charged in the chamber is increased by increasing a volume of space of the chamber, the duration period of a cooling operation may be improved. However, when the helmet worn by the user collides with a surrounding object or a falling object hits the helmet, a weight of the solidified PCM with an increased volume may bring about a hammer effect that causes a secondary blow to the user's head, which threatens a safety of the user.

Therefore, there is a need to develop a head cooling device that enhances a cooling effect by increasing a contact with the outer circumference surface of the user's head, increasing a duration period of a cooling operation by delaying the liquefaction of the PCM, and improves safety by protecting the user's head even when an impact is applied from outside.

The information included in this Background of the present disclosure is only for enhancement of understanding of the general background of the present disclosure and may not be taken as an acknowledgement or any form of suggestion that this information forms the prior art already known to a person skilled in the art.

SUMMARY

One aspect of the present disclosure is to provide a head cooling device that enhances a cooling effect by increasing a contact with an outer circumference surface of a user's head.

Another aspect of the present disclosure is to provide a head cooling device that increases a duration period of a cooling operation by delaying a liquefaction of the PCM to extend a replacement cycle thereof.

Still another aspect of the present disclosure is to provide a head cooling device that improves safety by protecting the user's head from an external impact.

Still further aspect of the present disclosure is to provide a head cooling device that is easily applied to various purposes with simple structural changes.

To accomplish the above-mentioned objects, a head cooling device according to a first embodiment of the present disclosure, which is charged with a phase change material (PCM) and performs a cooling function by seating on a user's head, may include: a central portion that has a predetermined volume of space, has a flange extending from an outer circumference thereof, and is seated on a top portion of the user's head; and a plurality of wing portions radially connected to the central portion via the flange and extending in a fan shape, wherein each of the wing portions includes a plurality of chambers each having a predetermined volume of space in which the PCM is charged and a plurality of bridges configured to partition and connect each of the plurality of chambers.

The central portion may be formed in a circular or polygonal shape having a predetermined volume of space, and the PCM may be filled in the respective spaces thereof.

The plurality of chambers in each wing portion may be formed by joining first and second sheets, and a volume of each chamber may increase in a radially outward direction from the central portion.

In a second embodiment of the present disclosure, the flange and the plurality of bridges may be formed in an arc shape by joining the first and second sheets, and wherein the flange and the plurality of bridges may be formed with a plurality of elongated holes in an arc shape to facilitate bending of each chamber.

In a third embodiment of the present disclosure, the central portion may be formed as an opening.

A head cooling device of a fourth embodiment according to another aspect of the present disclosure, which is charged with phase change material (PCM) and performs a cooling function by seating on a user's head, may include: a central portion that has a predetermined volume of space and is seated on a top portion of the user's head; a plurality of wing portions radially connected to the central portion and extending in a fan shape, wherein each of the wing portions includes a plurality of chambers having a predetermined volume of space in which the PCM is charged and a plurality of bridges configured to partition and connect each of the plurality of chambers, and wherein each of the plurality of chambers includes a cushioning member that absorbs and alleviates an external impact.

The central portion may be formed with a notch extending in a predetermined length therefrom and connected to adjacent wing portions.

The central portion may be filled with the PCM and further include a cushioning member in an inner space thereof.

The plurality of wing portions may include a flat first sheet, and a second sheet in which the plurality of chambers is pre-formed and joined to the first sheet.

The plurality of bridges may be formed by joining the first and second sheets, and may have a thickness to be bendable.

The first sheet may have a plurality of protrusions to ensure breathability on an opposite surface on which the second sheet is joined.

The plurality of wing portions may include a first sheet that is pre-formed with a portion of the space of each chamber, and a second sheet that is pre-formed with a residual portion of the space larger than that of the first sheet and is joined to the first sheet.

The plurality of chambers may have a cross section of which thickness is the same or different from each other.

The central portion and the plurality of chambers each may be filled with the PCM having the same or different melting points.

The cushioning member may be formed of non-frozen material that is not solidified at a solidification temperature of the PCM and may be coated with a waterproof film.

The cushioning member may include a foam material with cushioning properties to absorb impact, and an outer surface of the cushioning member may be coated with a waterproof film.

The head cooling device may further include a coupling member to be connected to the user's body, a helmet, or a cap.

A head cooling device of a fifth embodiment according to another aspect of the present disclosure, which is charged with phase change material (PCM) and performs a cooling function by seating on a user's head, may include: a central portion that has a predetermined volume of space and is seated on a top portion of the user's head; and a plurality of wing portions radially connected to the central portion where each of the wing portions includes first, second and third chambers each having a predetermined volume of space in which the PCM is charged and connected through first and second bridges configured to partition and connect the first to third chambers, respectively, wherein the central portion and each of the first, second and third chambers have a convex outer surface and include a cushioning member that absorbs and alleviates an external impact, and wherein the plurality of wing portions may include a first flat sheet, a second sheet that is pre-formed with a space of the central portion and each space of the first to third chambers, respectively and is joined to the first sheet, and a third sheet that is pre-formed with a space to accommodate the cushioning member and is joined to the third sheet.

In the central portion and the first, second, and third chambers, the cushioning member may be disposed in a space separated by a partition wall formed by the second and third sheets.

A head cooling device of a sixth embodiment according to another aspect of the present disclosure, which is charged with phase change material (PCM) and performs a cooling function by seating on a user's head, may include: a central portion that has a predetermined volume of space and is seated on a top portion of the user's head; a plurality of wing portions radially connected to the central portion and extending in a fan shape, wherein each of the wing portions includes a plurality of chambers having a predetermined volume of space in which the PCM is charged and a plurality of bridges configured to partition and connect each of the plurality of chambers, wherein each chamber includes a cushioning member that absorbs and alleviates an external impact, wherein an inner space of the central portion is divided into two spaces with a semicircular cross-section through a partition wall, each filled with the PCM and including a cushioning member, and wherein the plurality of wing portions is radially connected from the central portion in an even number, so that the head cooling device is foldable in half.

In the head cooling device according to the present disclosure, the plurality of chambers of each wing portion filled with the PCM may be easily bent through the bridge, thereby enhancing contact of respective chambers to the outer circumference surface of the user's head to increase the duration period of the cooling operation by the PCM.

In the head cooling device according to the present disclosure, since the cushioning member of the head cooling device is made of a foam material having numerous voids therein, the duration period of the cooling operation may be increased by delaying the liquefaction of the PCM due to an insulation effect of blocking heat transfer to the PCM.

The head cooling device according to the present disclosure may increase a charging amount of the PCM by increasing the volume of the chamber, thereby lengthening a replacement cycle by extending a usage time of the head cooling device.

In the head cooling device according to the present disclosure, since the cushioning member provided in the plurality of chambers includes a foam material with cushioning properties, it may protect the user's head and improve safety by absorbing and alleviating an impact applied from outside.

The head cooling device according to the present disclosure may be easily applied to various purposes by simply changing its shape and structure.

The methods and apparatuses of the present disclosure have other features and advantages which will be apparent from or are set forth in more detail in the accompanying drawings, which are incorporated herein, and the following Detailed Description, which together serve to explain certain principles of the present disclosure.

Figure 1:
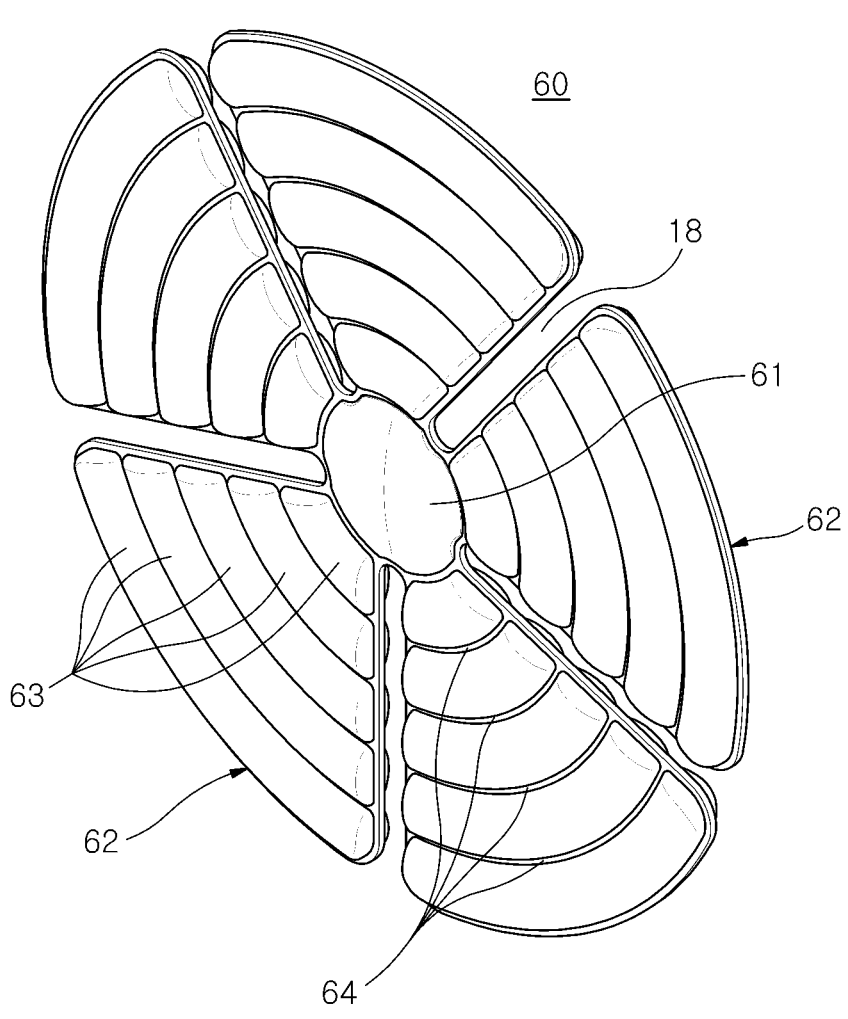
FIG. 1 is a perspective view schematically illustrating a head cooling device according to a first embodiment of the present disclosure.

The specific design features of the present disclosure as included herein, including, for example, specific dimensions, orientations, locations, and shapes will be determined in part by the particularly intended application and use environment.

In the figures, reference numbers refer to the same or equivalent parts of the present disclosure throughout the several figures of the drawing.

DETAILED DESCRIPTION OF THE INVENTION

Reference will now be made in detail to various embodiments of the present disclosure(s), examples of which are illustrated in the accompanying drawings and described below. While the present disclosure(s) will be described in conjunction with exemplary embodiments of the present disclosure, it will be understood that the present description is not intended to limit the present disclosure(s) to those exemplary embodiments of the present disclosure. On the other hand, the present disclosure(s) is/are intended to cover not only the exemplary embodiments of the present disclosure, but also various alternatives, modifications, equivalents and other embodiments, which may be included within the spirit and scope of the present disclosure as defined by the appended claims.

When a component, device, element, or the like of the present disclosure is described as having a purpose or performing an operation, function, or the like, the component, device, or element should be considered herein as being "configured to" meet that purpose or perform that operation or function. When a component is referred to as being "connected" to or "in contact" with another component, it should be understood that it may be directly connected to or in contact with the other component, but other components may exist therebetween. On the other hand, when a component is referred to as being "directly connected" to or "directly in contact" with another component, it should be understood that there is no other component therebetween.

In the following description and accompanying drawings, detailed descriptions of known functions or configurations that may obscure the gist of the present disclosure will be omitted. In addition, it should be noted that the same components throughout the drawings are indicated by the same reference numerals whenever possible.

Hereinafter, a head cooling device according to the present disclosure is described in detail with reference to the accompanying drawings. The head cooling device of the present disclosure may substantially have a disc shape and be charged with a phase change material (PCM) used in conventional cooling devices, and may perform a cooling function by being coupled to a helmet or cap or placed on a top portion of a user's head. Therefore, in describing the present disclosure, detailed descriptions of the known functions, configurations, or materials of the head cooling device will be omitted or briefly described to the extent necessary to clarify the gist of the present disclosure.

First Embodiment

FIG. 1 shows a head cooling device 60 according to a first embodiment of the present disclosure. The head cooling device 60 may include a central portion 61 that has a predetermined volume and is seated on a top portion of the user's head, and a plurality of wing portions 62 radially connected to the central portion 61 and extending in a fan shape, wherein each wing portion 62 includes a plurality of chambers 63 having a predetermined volume of space in which the PCM is filled, and a plurality of bridges 64 that partition and connect the plurality of chambers 63 to each other.

Figure 2:
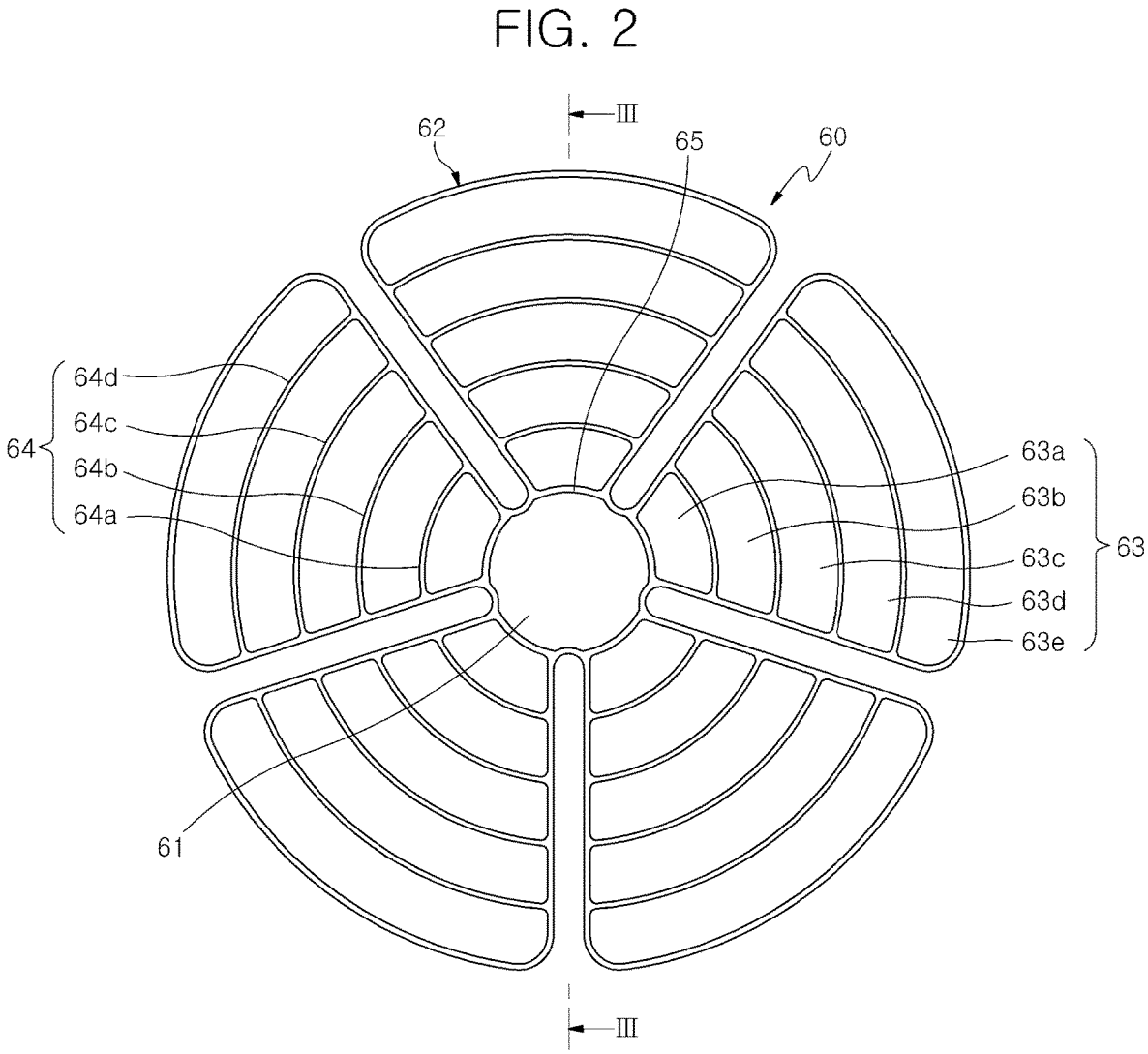
FIG. 2 is a plan view of FIG. 1.
Figure 3:
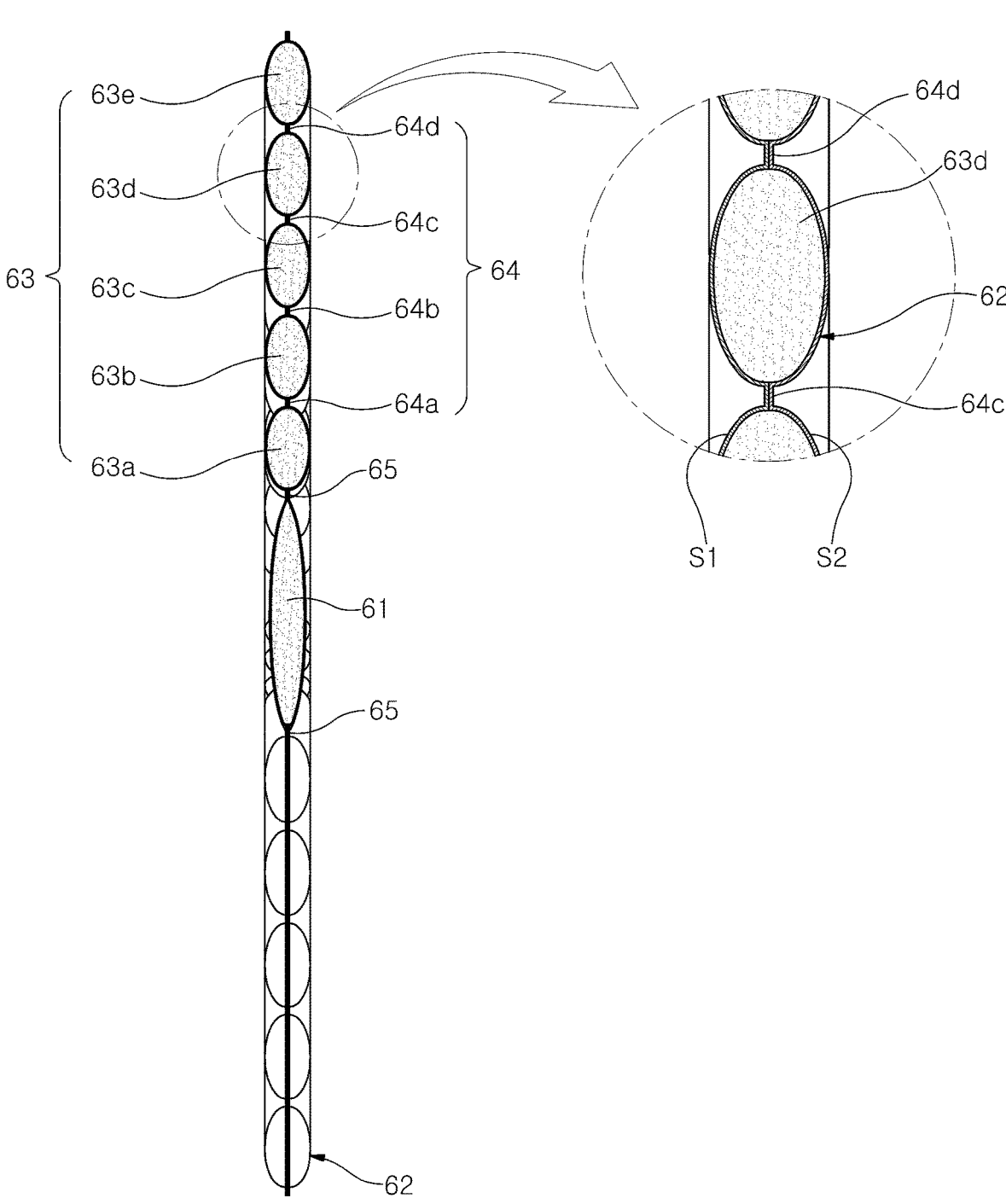
FIG. 3 is a cross-sectional view taken along line III-III in FIG. 2.

The plurality of chambers 63 provided in the respective wing portions 62 according to the first embodiment of the present disclosure may include, for example, five chambers, i.e., a first, a second, a third, a fourth, and a fifth chamber 63a, 63b, 63c, 63d, and 63e as shown in FIG. 2. In addition, the plurality of bridges 64 may include, for example, four bridges, i.e., a first, a second, a third, and a fourth bridge 64a, 64b, 64c, and 64d. However, the present disclosure may not be limited thereto, and the number of chambers 63 and bridges 64 may be increased or decreased respectively in response to the user's physical condition, use of the head cooling device 60, or the like.

In the first embodiment as shown in FIG. 1, the central portion 61 is illustrated as having a generally circular shape, but it may be formed in a polygonal shape such as a triangle, a square, a pentagon, or a hexagon with a predetermined volume of space. In addition, the PCM may be charged in an inner space of the central portion 61, thereby increasing the cooling effect on the top portion of the user's head.

As clearly shown in FIG. 2, the central portion 61 may be formed with a flange 65 having a predetermined width extending along its outer peripheral surface, and each first chamber 63a of the plurality of wing portions 62 may be connected to the flange 65, respectively.

Here, the first, second, third and fourth bridges 64a, 64b, 64c, and 64d and the flange 65 may be served as a hinge that allows each of the first, second, third, fourth and fifth chambers 63a, 63b, 63c, 63d, and 63e of the plurality of wing portions 62 to be sequentially bent downward from a top portion of the user's head along the outer circumference surface thereof to be in close contact with the user's head.

The head cooling device 60 according to the first embodiment of the present disclosure having the above configurations may be manufactured with a first sheet S1 and a second sheets S2 made of synthetic resin, for example, polyurethane using a mold (not shown) having a certain shape and a pattern. In other words, the central portion 61 in which the PCM is charged, the first, second, third, fourth and fifth chambers 63a, 63b, 63c, 63d, and 63e in which the PCM is charged, and the first, second, third, and fourth bridges 64a, 64b, 64c, and 64d disposed between the first, second, third, fourth and fifth chambers 63a, 63b, 63c, 63d, and 63e including the flange 65 may be formed through a one-time bonding operation using the mold.

Second Embodiment

Figure 4:
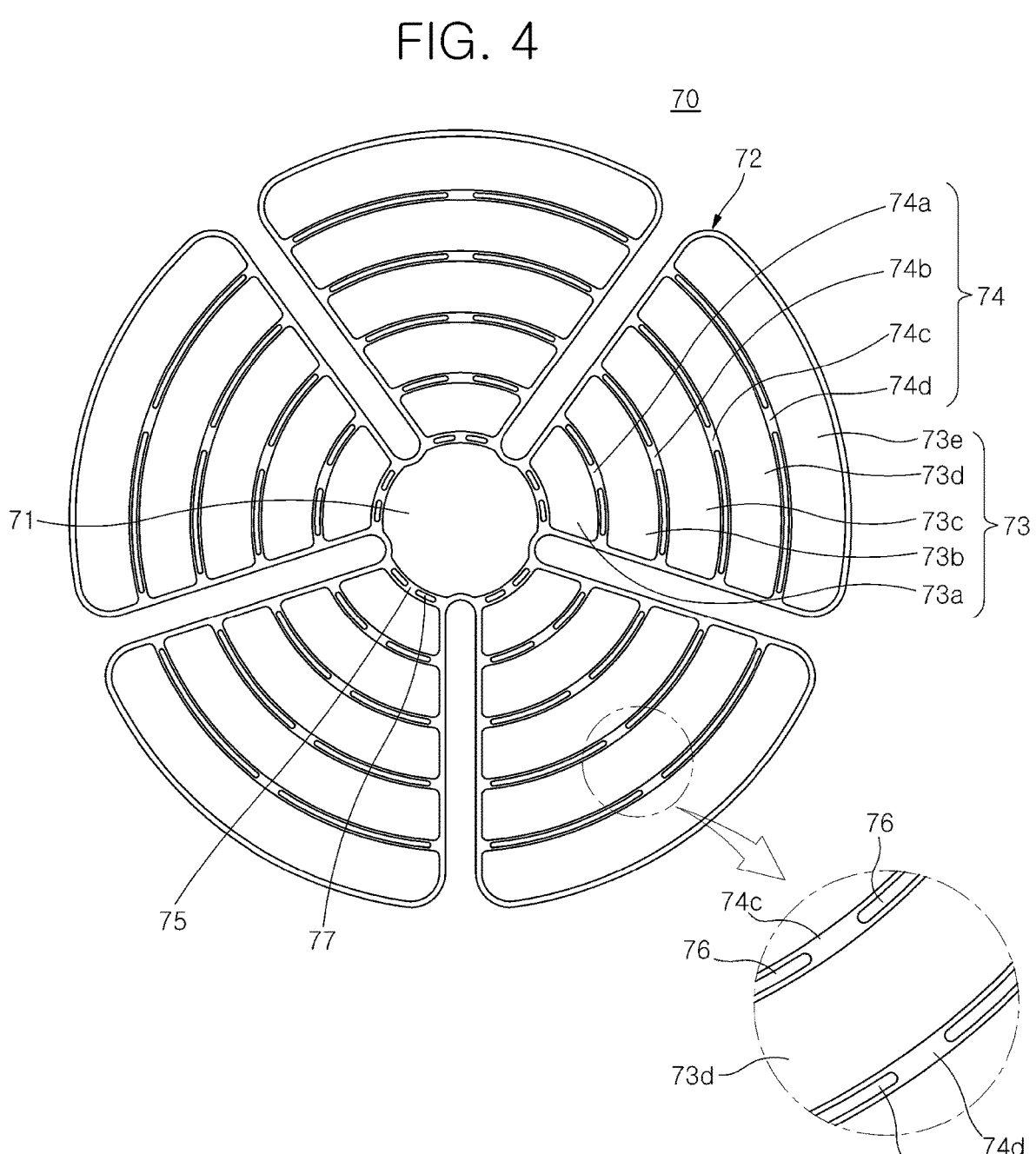
FIG. 4, which is similar to FIG. 2, is a plan view schematically illustrating a head cooling device according to a second embodiment of the present disclosure.

FIG. 4 shows a head cooling device 70 according to a second embodiment of the present disclosure. The head cooling device 70 may have almost the same configurations as the head cooling device 60 of the first embodiment, but a plurality of wing portions 72 filled with PCM is modified to improve contact with the user's head.

In other words, a plurality of wing portions 72 may be connected to a central portion 71 that sits on a top portion of the user's head. A plurality of arc-shaped elongated holes 76 is formed in the first, second, third, and fourth bridges 74a, 74b, 74c, and 74d disposed between the first, second, third, and fourth chambers 73a, 73b, 73c, 73d, and 73e provided in the wing portion 72, while a plurality of arc-shaped elongated holes 77 is formed in the flange 75, respectively.

Hence, in the head cooling device 70 according to the second embodiment of the present disclosure, the elongated holes 76 and 77 are configured to allow both the first, second, third, and fourth bridges 74a, 74b, 74c, and 74d and the flange 75 to be bent more easily, so the first, second, third, fourth, and fifth chambers 73a, 73b, 73c, 73d, and 73e, which are filled with the PCM, become easily in contact with the outer circumference of the user's head, improving the cooling effect.

Third Embodiment

Figure 5:
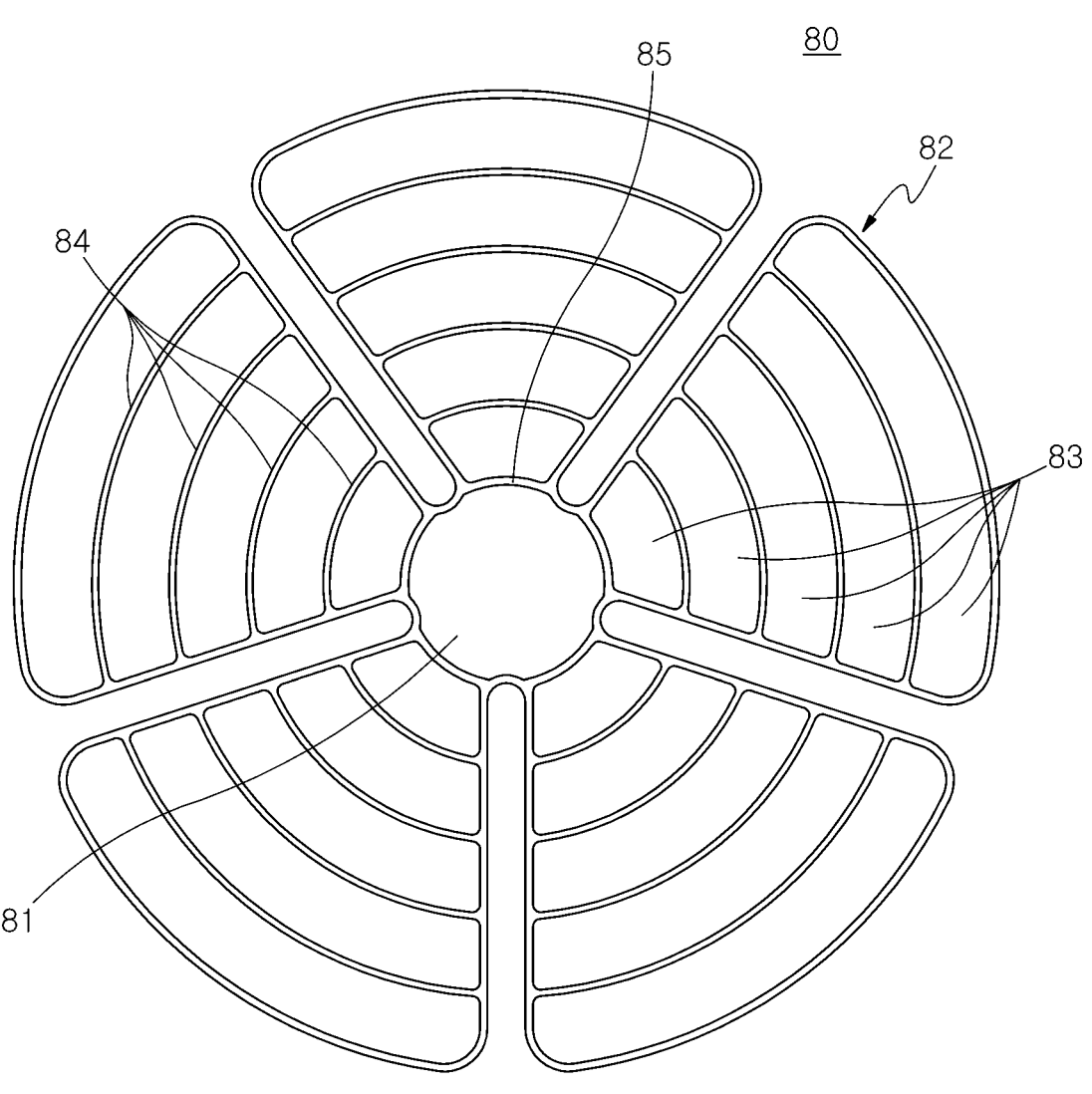
FIG. 5, which is similar to FIG. 2, is a plan view schematically illustrating a head cooling device according to a third embodiment of the present disclosure.

FIG. 5 shows a head cooling device 80 according to a third embodiment of the present disclosure. The head cooling device 80 may have almost the same configurations as the head cooling device 60 of the first embodiment, but there is a difference in that the central portion 61 of the first embodiment is modified to be formed as an opening 81.

That is, a plurality of wings 82 having a plurality of chambers 83 and a plurality of bridges 84 are radially connected around the opening 81 through a flange 85. Therefore, when the head cooling device 80 is seated on the user's head, the opening 81 to be located at the top portion of the user's head is configured to provide an air passage between the plurality of wing portions 82 each having the plurality of chambers 83 filled with the PCM, such that air may be smoothly flowing even through the opening 81, providing a better cooling effect than the head cooling device 60 in the first embodiment.

Fourth Embodiment

Figure 6:
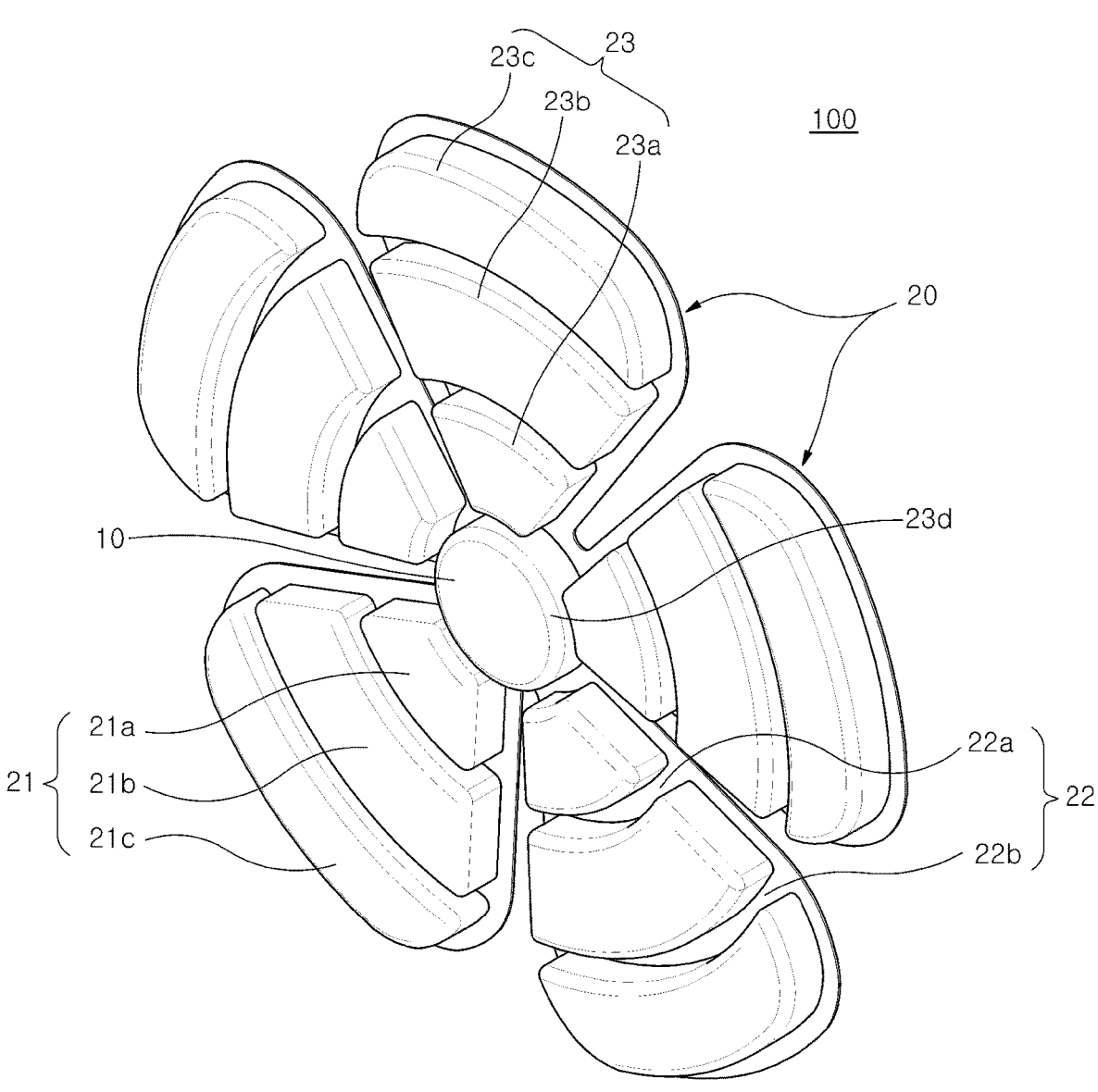
FIG. 6 is a perspective view schematically illustrating a head cooling device according to a fourth embodiment of the present disclosure.

FIG. 6 shows a head cooling device 100 according to a fourth embodiment of the present disclosure. The head cooling device 100 may have substantially similar configurations as the head cooling devices 60, 70 and 80 of the first to third embodiments of the present disclosure, but there is a difference in that an amount of the PCM to be charged is increased to improve the cooling effect, and additional means is provided to protect the user's head from an impact from outside.

The head cooling device 100 may include a central portion 10 that has a predetermined volume of space and is seated on a top portion of the user's head; a plurality of wing portions 20 radially connected to the central portion 10 and extending in a fan shape, wherein each of the wing portions 20 includes a plurality of chambers 21 having a predetermined volume of space in which the PCM is charged and a plurality of bridges 22 configured to partition and connect each of the plurality of chambers 21, and wherein each of the plurality of chambers 21 includes a cushioning member 23 that absorbs and alleviates an external impact.

Referring to FIG. 6, each of the plurality of wing portions 20 according to the fourth embodiment of the present disclosure may be illustrated to include three chambers, i.e., first, second, and third chambers 21a, 21b, and 21c, two bridges, i.e., first and second bridges 22a and 22b, and three cushioning members, i.e., first, second, and third cushioning members 23a, 23b, and 23c, respectively. However, the present disclosure may not be limited thereto, and the number of chambers 21, bridges 22, and cushioning members 23 may be increased or decreased depending on the user's physical condition, use of the head cooling device 100, or the like.

Figure 8:
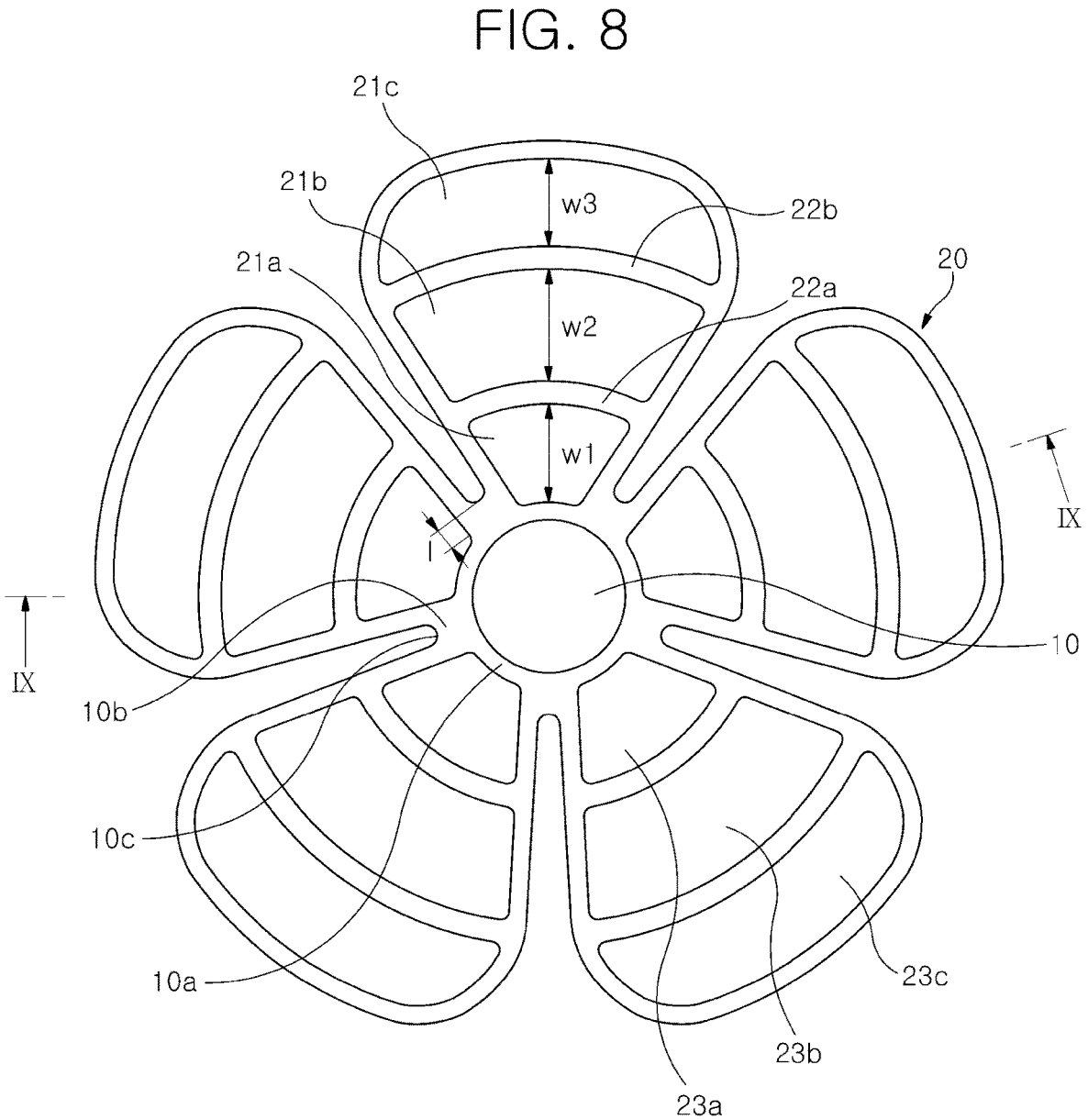
FIG. 8 is a plan view of FIG. 6
Figure 9A:
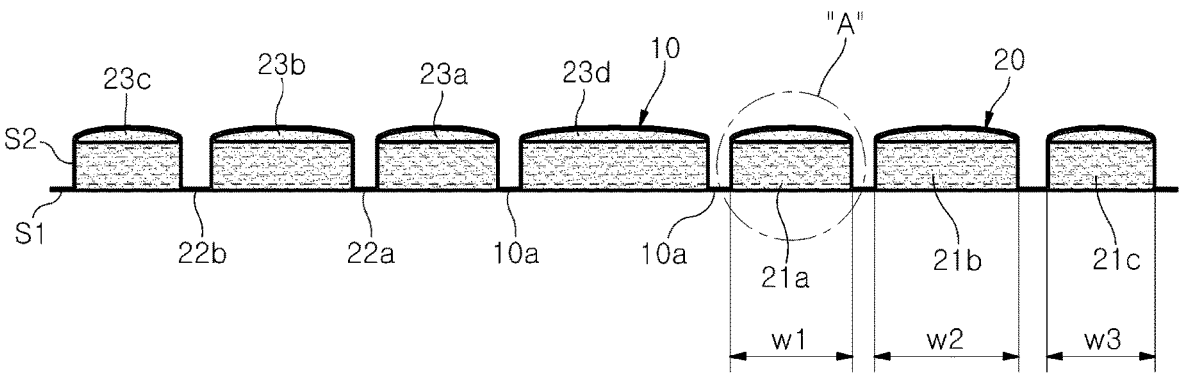
FIG. 9A is a cross-sectional view taken along line IX-IX of FIG. 8.

As shown in FIGS. 8 and 9A, the first, second, and third chambers 21a, 21b, and 21c each may be formed in an arc shape having a width w1, w2, and w3 in a radial direction, but my not be limited thereto. Here, the width w1, w2, and w3 of the first, second, and third chambers 21a, 21b, and 21c in the radial direction may be set to have the same width or different widths, respectively.

The central portion 10 according to the fourth embodiment of the present disclosure is illustrated as having a circular shape, but may be formed in a polygonal shape such as a triangle, a square, a pentagon, or a hexagon with a predetermined volume of space.

Meantime, the central portion 10 may be filled the PCM in an inner space thereof to increase the cooling effect on the top portion of the user's head, and the central portion 10 may be further provided with a cushioning member 23d to protect the top portion of the user's head from an impact applied from outside.

The central portion 10, as clearly shown in FIG. 8, may include a flange 10a having a predetermined width extending along an outer peripheral surface thereof, and each first chamber 21a of the plurality of the wing portions 20 may be connected to the flange 10a.

According to the fourth embodiment of the present disclosure, as shown in FIGS. 6 and 8, a notch 10b may be further formed to extend in a predetermined length between the flange 10a of the central portion 10 and adjacent wing portions 20, where the notch 10b is connected to adjacent wing portions 20 to provide a rigidity thereto for maintaining an arrangement shape of the wing portions 20, while not impairing a bendability of each wing portion 20.

In other words, the notch 10b may connect each first chambers 21a of adjacent wing portions 20 to each other to reinforce a rigidity thereof, thereby supporting an unfolded state of each wing portion 20 to maintain its shape. Here, the notch 10b may have a concave portion 10c on its outer peripheral surface. It is desirable that the length 1 of the notch 10b extending from the flange 10a does not exceed ½ of the width w1 of the first chamber 21a, but is not limited thereto.

Figure 7:
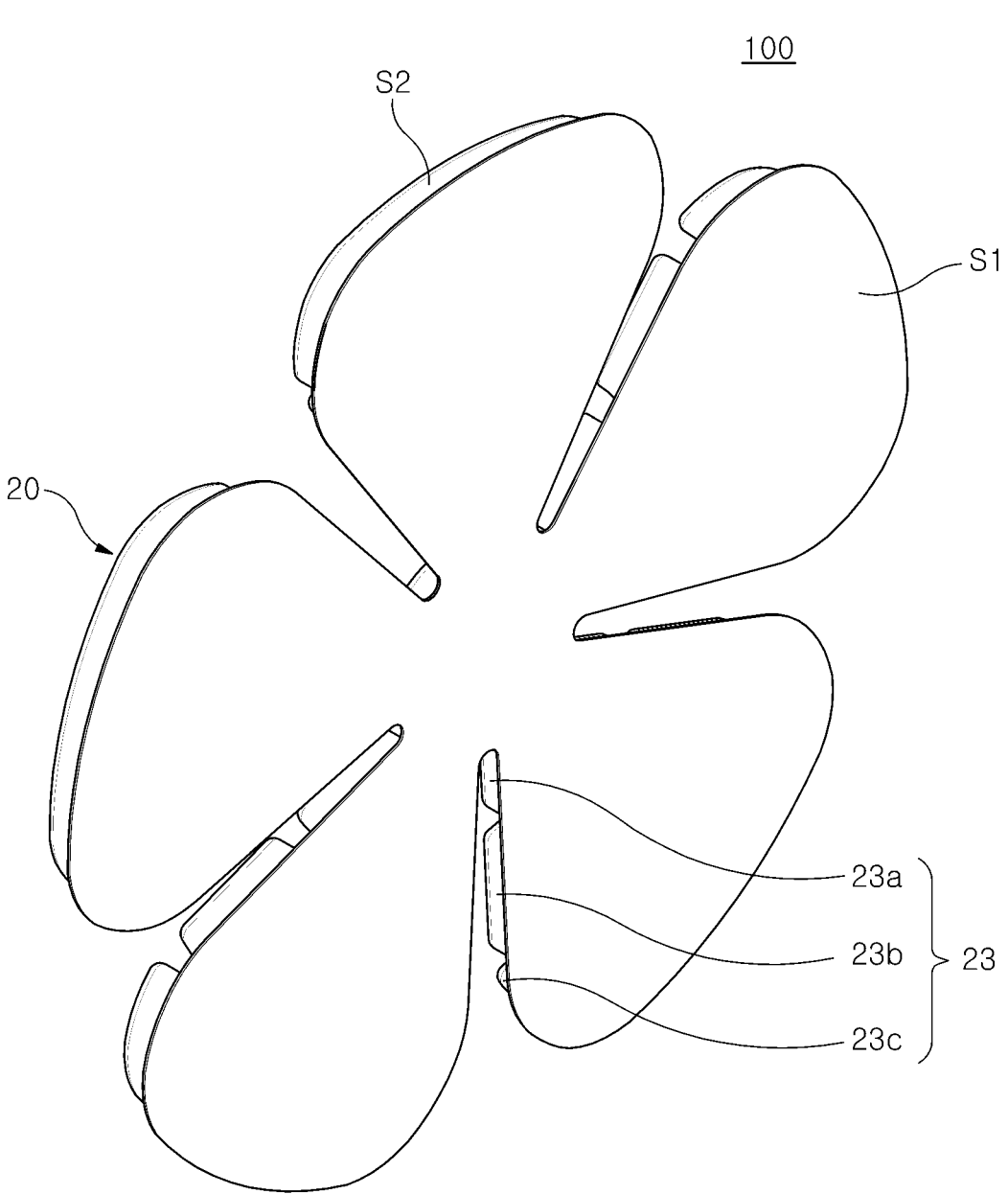
FIG. 7 is a bottom perspective view of FIG. 6
Figure 9B:
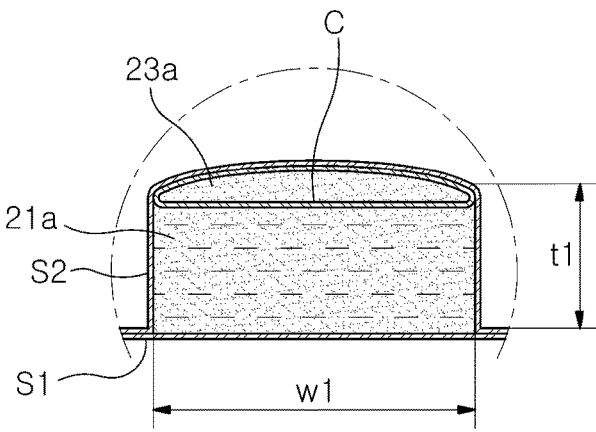
FIG. 9B is an enlarged cross-sectional view of portion "A" in FIG. 9A.

As shown in FIGS. 7, 9A, and 9B, the plurality of wing portions 20 of the present disclosure may be formed by joining a first sheet S1 having a flat surface and contacting the user's head, and a second sheet S2 where a central portion 10 and a plurality of first, second, and third chambers 21a, 21b, and 21c each having a space of the predetermined volume have been previously formed. Here, the first and second sheets S1 and S2 may be made of synthetic resin with proper formability, a tear resistance and a tensile strength, preferably polyurethane, but are not limited thereto.

Since the first chamber 21a may be filled with the PCM in a pressurized state, upper and lower outer peripheral surfaces of the first chamber 21a may have convex surfaces after the PCM is filled. Likewise, upper and lower outer peripheral surfaces of the central portion 10 and the second and third chambers 21b, and 21c also may have convex surfaces.

Meanwhile, the first and second sheets S1 and S2 may be joined by using a mold (not shown) with a predetermined configurations corresponding to the head cooling device 100 in a high-frequency bonding or a heat melt bonding process, wherein the flange 10a and the notch 10b of the central portion 10 and the first and second bridges 22a and 22b between the first, second and third chambers 21a, 21b and 21c may be formed simultaneously or separately to each other. Hence, the first, second, and third chambers 21a, 21b and 21c may be partitioned and separated from each other by the first and second bridges 22a and 22b.

The first and second bridges 22a and 22b may serve as hinges that bendably connect the first, second and third chambers 21a, 21b and 21c to each other. The first, second and third chambers 21a, 21b and 21c may be easily bent along the outer circumference surface of the user's head by means of the first and second bridges 22a and 22b, realizing maximum contact to the user's head with increased contacts, thereby improving the cooling effect.

Here, the thickness of the first and second bridges 22a and 22b may correspond to just the thickness of the first and second sheets S1 and S2 being joined to each other, but may be increased or decreased to adjust a degree of bending of the first, second, and third chambers 21a, 21b, and 21c with respect to the user's head.

Figure 9C:
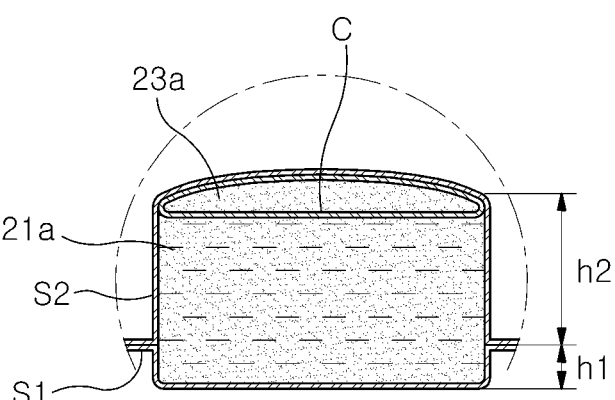
FIG. 9C is an enlarged cross-sectional view illustrating a modification in which a portion of a chamber is previously formed in a first sheet.

Meanwhile, as a modified embodiment of the present disclosure, as shown in FIG. 9C, the first and second sheets S1 and S2 may be formed to have certain configurations and joined by a high-frequency bonding or a heat melt bonding process, wherein the first sheet S1 is concavely formed with a height h2 having a partial volume of the first, second and third chambers 21a, 21b, and 21c, and the second sheet S2 is concavely formed with a height h2 having a remaining volume of the first, second and third chambers 21a, 21b, and 21c.

Therefore, when the head cooling device 100 of the present disclosure is seated on the user's head, the first, second, and third chambers 21a, 21b, and 21c formed in the first sheet S1, which face the user's head and have certain volumes of space, protrude at the height h1 toward the user's head, forming ventilation passages therebetween. Accordingly, air may flow through the ventilation passages, thereby improving the cooling effect on the user's head.

Figure 9D:
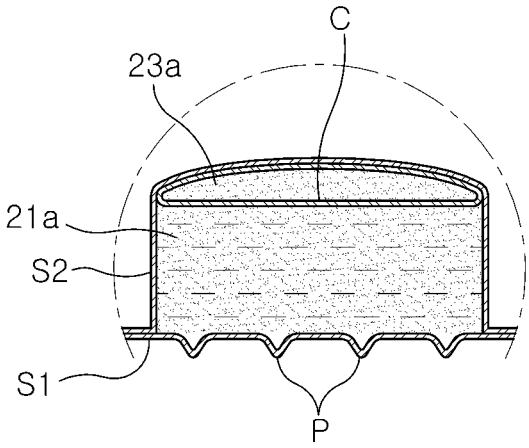
FIG. 9D is an enlarged cross-sectional view illustrating a modification in which a plurality of projections are formed on a lower surface of the first sheet.

As a modified embodiment of the present disclosure, as shown in FIG. 9D, a plurality of protrusions P may be formed on a lower surface of the first sheet S1 to form ventilation passages through which air flows to increase the cooling effect.

In addition, each of the plurality of chambers 21a, 21b, and 21c may have a cross section with the same thickness and width, for example, as a thickness t1 and a width w1 of the first chamber t1 as shown in FIG. 9B. However, as a modified example of the present disclosure, each of the first, second, and third chambers 21a, 21b, and 21c may have the cross section with a different thickness or width, respectively.

Figure 10A:
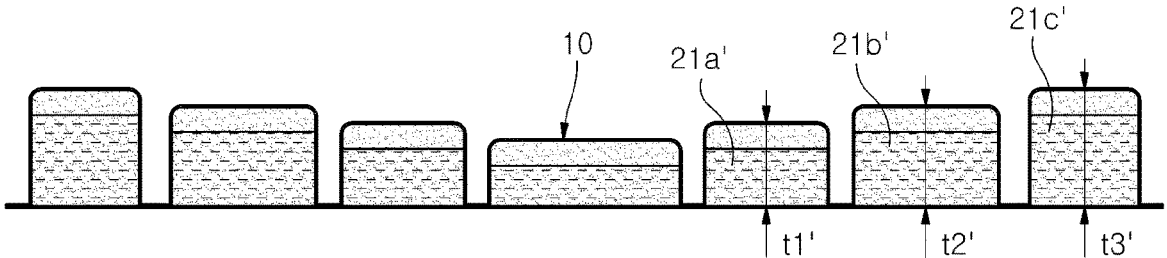
FIG. 10A is a cross-sectional view illustrating an embodiment in which a thickness of the plurality of chambers of FIG. 9 increases in an outward direction from a central portion of the head cooling device.
Figure 10B:
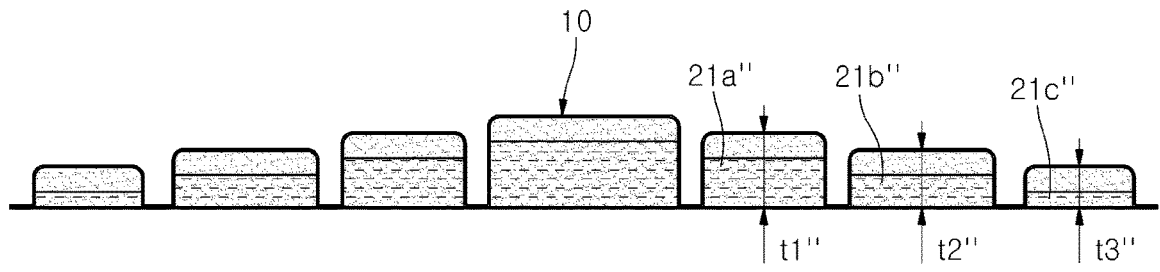
FIG. 10B is a cross-sectional view illustrating an embodiment in which a thickness of the plurality of chambers of FIG. 9 decreases in an outward direction from a central portion of the head cooling device.

For example, as shown in FIG. 10A, each of the first, second, and third chambers 21a', 21b', and 21c' may have a cross section with a thickness t1', t2', and t3' which increases gradually outward from the central portion 10. In contrast, as shown in FIG. 10B, each of the first, second, and third chambers 21a", 21b", and 21c" may have a thickness t1", t2", and t3" which decreases gradually outward from the central portion 10.

In the present disclosure, the PCM to be filled in the plurality of chambers 21 may have hydrocarbon-based organic materials including Tetradecane, Hexadecane, Heptadecane, Octadecane, Nanodecane, etc., and other inorganic materials. Since chemical compositions and properties thereof are well known in the art, detailed descriptions thereof will be omitted.

The cushioning member 23 of the present disclosure may be a non-frozen or anti-freezing material that does not solidify at the solidification temperature of the PCM. The cushioning member 23 made of a non-frozen material may be coated with a waterproof film C as shown in FIG. 9B. The non-frozen material may include, for example, air, water, or a material harmless to the human body in a gel or sol state.

Meanwhile, the cushioning member 23 of the present disclosure may include a foam material with cushioning properties to absorb impact, for example, a sponge containing many porosities or voids therein.

Here, as shown in FIG. 9C, the cushioning member 23 made of the foam material is coated with a waterproof film C to surround its outer surface to prevent the PCM in a liquid state from seeping into the pores of the foam material, maintaining its cushioning properties that absorbs impact.

In addition, the cushioning member 23 may provide an insulating effect in which the internal pores of the foam material reduce or block heat transfer to the PCM filled in the chambers 21, thereby delaying liquefaction of the PCM and increasing the duration period of a cooling operation.

Meanwhile, the central portion 10 and the first, second, and third chambers 21a, 21b, and 21c of the present disclosure may be filled with a PCM having the same melting point (solidification point).

However, as a modified example of the present disclosure, the central portion 10 and the first, second, and third chambers 21a, 21b, and 21c each may be filled with a PCM having different melting points in consideration of the cooling effect on the user's head.

In other words, the central portion 10 and the first chamber 21a, which are close in contact with the top portion of the user's head, where a temperature of the user's head is presumably to be the highest, may be filled with a PCM with a high melting point, for instance, Octadecane with a melting point of 28° C., so that at temperatures below 28° C., the PCM maintains its solidified state to maintain a long duration period of a cooling operation. In contrast, the second and third chambers 21b and 21c in contact with the outer side of the top portion of the user's head may be filled with a PCM with a relatively lower melting point, such as Hexadecane with a melting point of 18° C., Heptadecane with a melting point of 22° C., or Tetradecane with a melting point of 5.5° C. Alternatively, on the contrary, a PCM with a lower melting point may be sequentially filled in the chambers 21 toward the central portion 10, respectively.

Fifth Embodiment

Figure 11A:
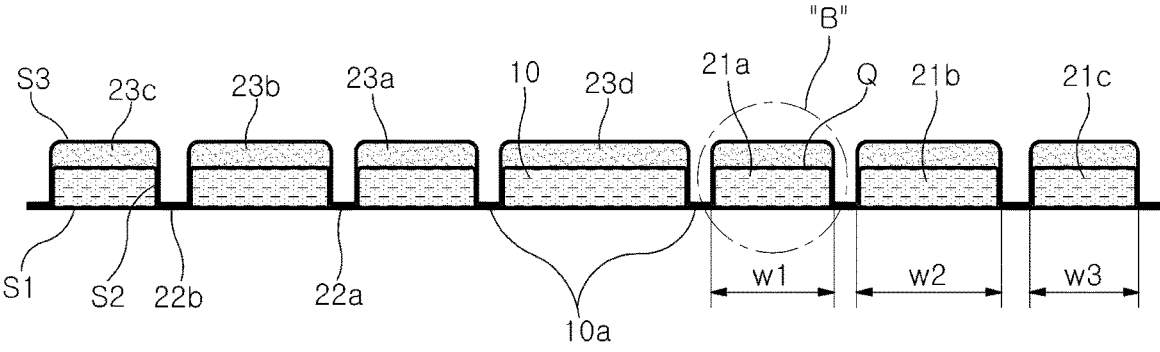
FIG. 11A, which is similar to FIG. 9A, is a cross-sectional view illustrating a head cooling device according to a fifth embodiment of the present disclosure in which a plurality of chambers are formed using first, second, and third sheets.
Figure 11B:
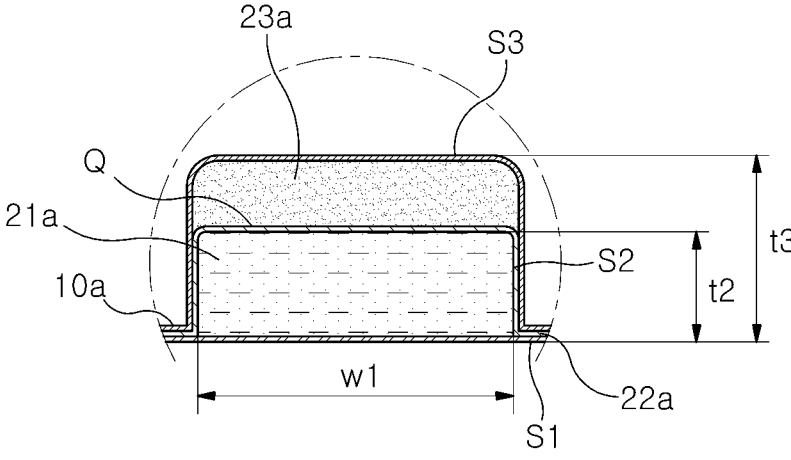
FIG. 11B is an enlarged cross-sectional view of portion "B" in FIG. 11A.

FIGS. 11A and 11B show a head cooling device according to a fifth embodiment of the present disclosure which may have substantially similar configurations as the head cooling device 100 of the fourth embodiment of the present disclosure, but there is a difference in that a head cooling device is manufactured by joining three sheets, a first sheet S1, a second sheet S2 and a third sheet S3. For convenience and simplicity of explanation, the same reference numerals as those in FIGS. 6 to 8 will be used.

Referring to FIG. 11A, a plurality of wing portions 20 of the present disclosure may be formed by joining a flat first sheet S1, a second sheet S2 which is pre-formed to have a space with a thickness t2 to accommodate a central portion 10 having a space of a circular cross-section and arc-shaped first, second, and third chambers 21a, 21b, and 21c, respectively and is joined to the first sheet S1, and a third sheet S3 which is pre-formed to have a space with a thickness t3 to accommodate the second sheet S2 and cushioning members 23a, 23b, 23c, and 23d which are disposed over the second sheet S2, respectively, and is joined to the second sheet (S2).

Here, each of the cushioning members 23a, 23b, 23c, and 23d is positioned in an independent space formed by the second and third sheets S2 and S3 and separated by a partition wall Q. Accordingly, since the cushioning members 23a, 23b, 23c, and 23d have no risk of penetration of the PCM in a liquid state, there is no need to coat the cushioning members 23a, 23b, 23c, and 23d with a waterproof film C, as in the fourth embodiment shown in FIGS. 9A and 9B.

Meanwhile, the head cooling device 60, 70, 80, and 100 of the present disclosure described above may include additional member for coupling to the user's body, helmet, or cap. For convenience of explanation, the head cooling device 100 of the fourth embodiment will be used as an example.

Figure 12:
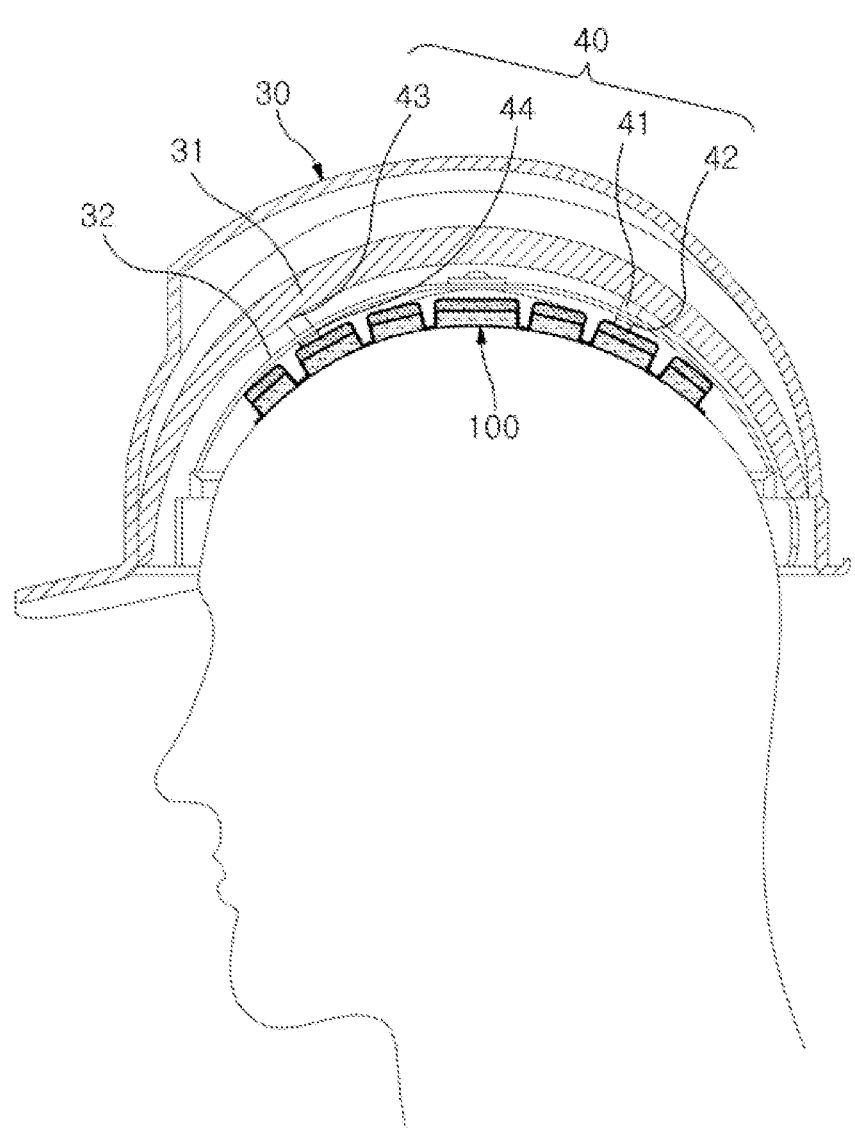
FIG. 12 is a schematic cross-sectional view illustrating a state in which a head cooling device according to the fourth embodiment of the present disclosure is seated on a user's head by being coupled to a helmet.

Referring to FIG. 12, a coupling member 40 of the present disclosure may include a hook-and-loop fastener, or a Velcro® brand fastener. For example, at least one loop fastener 41 is provided at bands 32 which are arranged crosswise to contact the user's head under a shock absorber 31 inside the helmet 30. In addition, at least one hook fastener 42 is provided preferably at the central portion 10 or at the plurality of wing portions 20. By fastening the loop fastener 41 and the hook fastener 42 to each other, the head cooling device 100 according to the fifth embodiment of the present disclosure may be securely coupled to the helmet 30 and brought into close contact with the user's head.

In addition, as a modified example of the present disclosure, instead of the hook-and-loop fasteners 42 and 41, at least one pair of permanent magnets 43 and 44 with different poles may be applied. For example, as shown in FIG. 12, at least one permanent magnet 43 with one polarity is provided at the band 32 of the helmet 30, and at least one permanent magnet of different polarity is provided on the plurality of wing portions 20. Accordingly, the head cooling device 100 may be coupled to the helmet 30 by the magnetic force of the permanent magnets 43 and 44.

Figure 13:
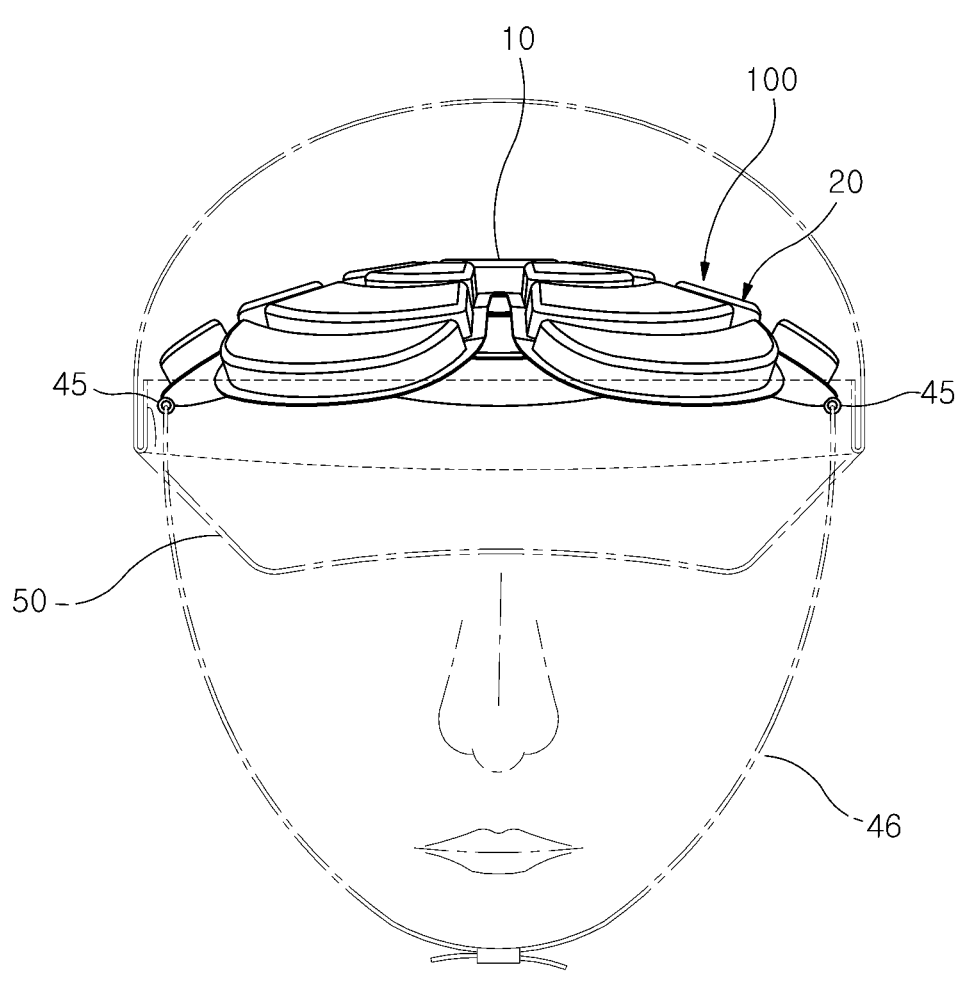
FIG. 13 is a schematic perspective view illustrating a state in which a head cooling device according to the fourth embodiment of the present disclosure is seated on a user's head by being coupled to a cap.

Alternatively, the head cooling device 100 of the present disclosure may be applied to a conventional cap, such as a baseball cap 50, not a helmet (30) as shown in FIG. 13.

Referring to FIG. 13, a coupling ring 45 is formed at an outer periphery of at least two wing portions 20 of the head cooling device 60, 70, 80 and 100 of the present disclosure, for example, the head cooling device 100 according to the fifth embodiment of the present disclosure, while a pair of tightening strings 46 is coupled with the coupling rings 45. In use, the hair cooling device 100 is seated on the top portion of the user's head, and then the opposite tightening strings 46 are pulled and tied, and then the head cooling device 100 becomes firmly and tightly in contact with the user's head, so the user may obtain a cooling effect even while wearing a baseball cap, a work cap, or women's hat, etc.

Sixth Embodiment

Figure 14:
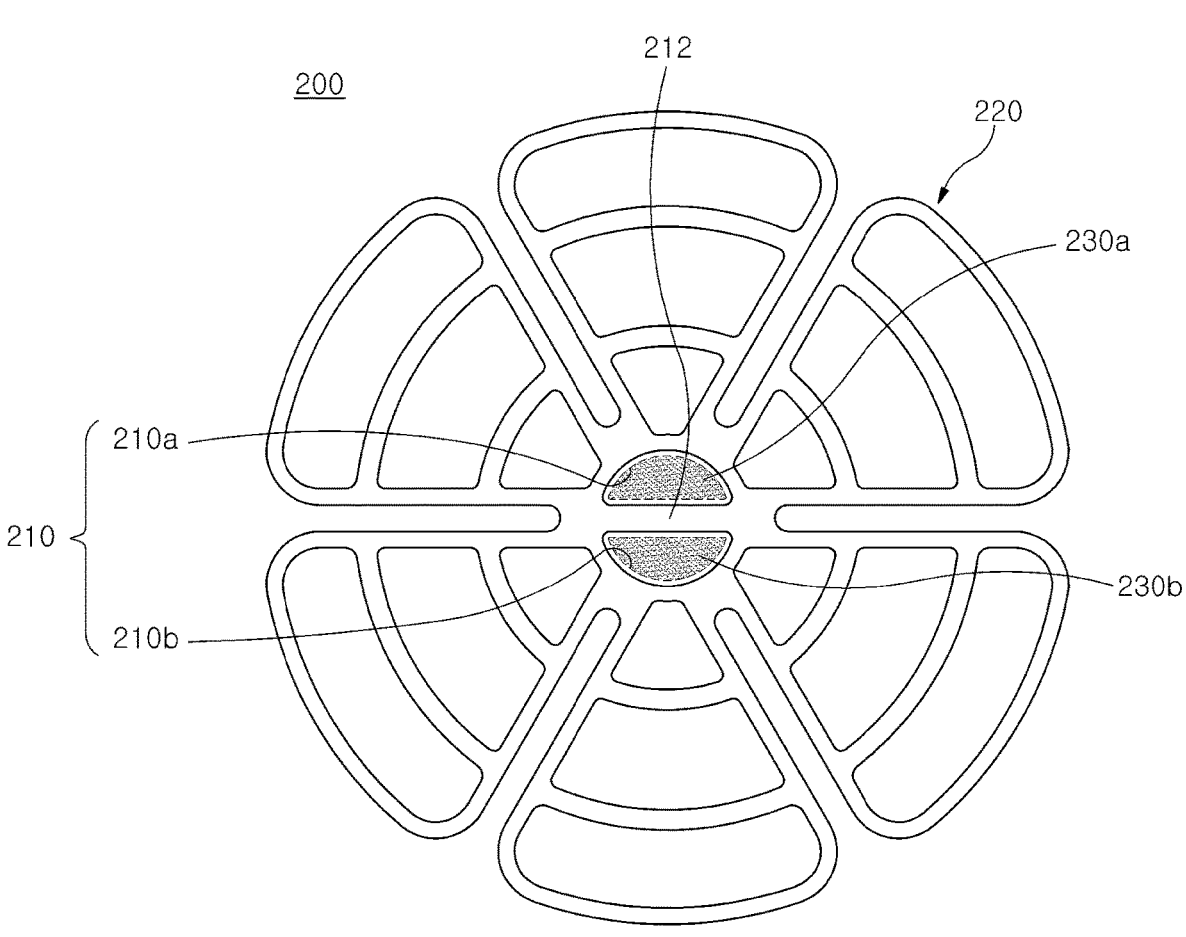
FIG. 14, which is similar to FIG. 8, is a plan view illustrating a head cooling device according to a sixth embodiment of the present disclosure which may be folded in half.

FIG. 14 shows a head cooling device 200 according to a sixth embodiment of the present disclosure. The head cooling device 200 may have substantially similar configurations as the head cooling device 100 of the fourth embodiment of the present disclosure, but there is a difference in configurations for easy transportation and storage.

That is, an internal space of the central portion 210 may be divided into two semicircular cross-sectional spaces 210a and 210b with a partition wall 212 at a center thereof. Each of the spaces 210a and 210b may be filled with the PCM and have cushioning member 230a and 230b therein, respectively. The wing portions 220 may be formed in an even number, such as 2, 4, 6, 8, 10, etc., to reduce a space to occupy by folding the head cooling device 200 in half.

For example, in the embodiment shown in FIG. 14, it is illustrated that six wing portions 220 are radially connected from the central portion 210, so the head cooling device 200 may be folded exactly in half, reducing a space to be occupied to improve convenience in carrying, packaging or transportation thereof.

For convenience in explanation and accurate definition in the appended claims, the terms "upper", "lower", "inner", "outer", "up", "down", "upwards", "downwards", "front", "rear", "back", "inside", "outside", "inwardly", "outwardly", "interior", "exterior", "internal", "external", "forwards", and "backwards" are used to describe features of the exemplary embodiments with reference to the positions of such features as displayed in the figures. It will be further understood that the term "connect" or its derivatives refer both to direct and indirect connection.

The term "and/or" may include a combination of a plurality of related listed items or any of a plurality of related listed items. For example, "A and/or B" includes all three cases such as "A", "B", and "A and B".

In the present specification, unless stated otherwise, a singular expression includes a plural expression unless the context clearly indicates otherwise.

In exemplary embodiments of the present disclosure, "at least one of A and B" may refer to "at least one of A or B" or "at least one of combinations of at least one of A and B". Furthermore, "one or more of A and B" may refer to "one or more of A or B" or "one or more of combinations of one or more of A and B".

In the exemplary embodiment of the present disclosure, it should be understood that a term such as "include" or "have" is directed to designate that the features, numbers, steps, operations, elements, parts, or combinations thereof described in the specification are present, and does not preclude the possibility of addition or presence of one or more other features, numbers, steps, operations, elements, parts, or combinations thereof.

The foregoing descriptions of specific exemplary embodiments of the present disclosure have been presented for purposes of illustration and description. They are not intended to be exhaustive or to limit the present disclosure to the precise forms disclosed, and obviously many modifications and variations are possible in light of the above teachings. The exemplary embodiments were chosen and described in order to explain certain principles of the invention and their practical application, to enable others skilled in the art to make and utilize various exemplary embodiments of the present disclosure, as well as various alternatives and modifications thereof. It is intended that the scope of the present disclosure be defined by the Claims appended hereto and their equivalents.

What is claimed is:

1. A head cooling device, which is charged with a phase change material (PCM) and performs a cooling function by seating on a user's head, the head cooling device comprising:
   a central portion that has a predetermined volume of space, has a flange extending from an outer circumference thereof, and is seated on a top portion of the user's head when in use; and
   a plurality of wing portions radially connected to the central portion via the flange and extending in a fan shape,
   wherein each of the wing portions includes a plurality of chambers each having a predetermined volume of space in which the PCM is charged, and a plurality of bridges configured to partition and connect each of the plurality of chambers,
   wherein each of the plurality of bridges is configured to partition and separate the plurality of chambers from each other, and to define each of the plurality of chambers as a closed space that does not allow the PCM to flow to an adjacent chamber across each bridge, and
   wherein each of the plurality of bridges is configured to serve as a hinge that allows each of the plurality of chambers of the plurality of wing portions to be sequentially bent downward from the top portion of the user's head along an outer circumference surface thereof so as to be in close contact with the user's head when in use, thereby improving a cooling effect.

2. The head cooling device of claim 1, wherein the central portion is formed in a circular or polygonal shape having a predetermined volume of space, and the PCM is filled in the respective spaces thereof.

3. The head cooling device of claim 1, wherein the plurality of chambers in each wing portion is formed by joining a first sheet and a second sheet, and a volume of each chamber increases in a radially outward direction from the central portion.

4. The head cooling device of claim 3, wherein the flange and the plurality of bridges are formed in an arc shape by joining the first and second sheets, and, wherein the flange and the plurality of bridges are formed with a plurality of elongated holes in an arc shape to facilitate bending of each chamber.

5. The head cooling device of claim 1, wherein the central portion is formed as an opening.

6. A head cooling device, which is charged with a phase change material (PCM) and performs a cooling function by seating on a user's head, the head cooling device comprising:
   a central portion that has a predetermined volume of space and is seated on a top portion of the user's head when in use;
   a plurality of wing portions radially connected to the central portion and extending in a fan shape,
   wherein each of the wing portions includes a plurality of chambers having a predetermined volume of space in which the PCM is charged, and a plurality of bridges configured to partition and connect each of the plurality of chambers, and
   wherein each of the plurality of chambers includes a cushioning member that absorbs and alleviates an external impact,
   wherein the plurality of wing portions includes a first sheet that is pre-formed with a portion of the space of each chamber, and a second sheet that is pre-formed with a residual portion of the space larger than that of the first sheet and is joined to the first sheet.

7. The head cooling device of claim 6, wherein the central portion is formed with a notch extending in a predetermined length therefrom and connected to adjacent wing portions.

8. The head cooling device of claim 6, wherein the central portion is filled with the PCM and further includes a cushioning member in an inner space thereof.

9. The head cooling device of claim 8, wherein the central portion and the plurality of chambers each is filled with the PCM having the same or different melting points.

10. The head cooling device of claim 8, wherein the cushioning member is formed of non-frozen material that is not solidified at a solidification temperature of the PCM and is coated with a waterproof film.

11. The head cooling device of claim 8, wherein the cushioning member includes a foam material with cushioning properties to absorb impact, and an outer surface of the cushioning member is coated with a waterproof film.

12. The head cooling device of claim 6, wherein the plurality of wing portions include a flat first sheet, and a second sheet in which the plurality of chambers is pre-formed and joined to the first sheet.

13. The head cooling device of claim 12, wherein plurality of bridges is formed by joining the first and second sheets, and has a thickness to be bendable.

14. The head cooling device of claim 12, wherein the first sheet has a plurality of protrusions to ensure breathability on an opposite surface on which the second sheet is joined.

15. The head cooling device of claim 6, wherein the plurality of chambers has a cross section of which thickness is the same or different from each other.

16. The head cooling device of claim 6, wherein the head cooling device further includes a coupling member to be connected to the user's body, a helmet, or a cap.

17. A head cooling device, which is charged with a phase change material (PCM) and performs a cooling function by seating on a user's head, the head cooling device comprising:

a central portion that has a predetermined volume of space and is seated on a top portion of the user's head when in use; and a plurality of wing portions radially connected to the central portion where each of the wing portions includes first, second and third chambers each having a predetermined volume of space in which the PCM is charged and connected through first and second bridges configured to partition and connect the first to third chambers, respectively, wherein the central portion and each of the first, second and third chambers have a convex outer surface and include a cushioning member that absorbs and alleviates an external impact, and wherein the plurality of wing portions includes a first flat sheet, a second sheet that is pre-formed with a space of the central portion and each space of the first to third chambers, respectively and is joined to the first sheet, and a third sheet that is pre-formed with a space to accommodate the cushioning member and is joined to the third sheet.

18. The head cooling device of claim 17, wherein in the central portion and the first, second, and third chambers, the cushioning member is disposed in a space separated by a partition wall formed by the second and third sheets.

19. A head cooling device, which is charged with a phase change material (PCM) and performs a cooling function by seating on a user's head, the head cooling device comprising:

a central portion that has a predetermined volume of space and is seated on a top portion of the user's head when in use; and a plurality of wing portions radially connected to the central portion and extending in a fan shape, wherein each of the wing portions includes a plurality of chambers having a predetermined volume of space in which the PCM is charged and a plurality of bridges configured to partition and connect each of the plurality of chambers, wherein each chamber includes a cushioning member that absorbs and alleviates an external impact, wherein an inner space of the central portion is divided into two spaces with a semicircular cross-section through a partition wall, each filled with the PCM and including a cushioning member, and wherein the plurality of wing portions is radially connected from the central portion in an even number, so that the head cooling device is foldable in half.

* * * * *